(12) United States Patent
Peine

(10) Patent No.: US 11,529,202 B2
(45) Date of Patent: Dec. 20, 2022

(54) SYSTEMS AND METHODS FOR CONTROLLING A CAMERA POSITION IN A SURGICAL ROBOTIC SYSTEM

(71) Applicant: Covidien LP, Mansfield, MA (US)

(72) Inventor: William Peine, Ashland, MA (US)

(73) Assignee: COVIDIEN LP, Mansfield, MA (US)

( * ) Notice: Subject to any disclaimer, the term of this patent is extended or adjusted under 35 U.S.C. 154(b) by 275 days.

(21) Appl. No.: 16/996,236

(22) Filed: Aug. 18, 2020

(65) Prior Publication Data

US 2020/0375673 A1    Dec. 3, 2020

Related U.S. Application Data

(63) Continuation of application No. 15/310,476, filed as application No. PCT/US2015/029427 on May 6, 2015, now Pat. No. 10,743,947.

(60) Provisional application No. 61/993,379, filed on May 15, 2014.

(51) Int. Cl.
*A61B 34/30* (2016.01)
*A61B 90/00* (2016.01)
*A61B 34/00* (2016.01)

(52) U.S. Cl.
CPC .............. *A61B 34/30* (2016.02); *A61B 34/74* (2016.02); *A61B 90/361* (2016.02); *A61B 2034/742* (2016.02)

(58) Field of Classification Search
CPC ......... A61B 34/30; A61B 34/37; A61B 34/70; A61B 34/74; A61B 90/361; A61B 2034/742
See application file for complete search history.

(56) References Cited

U.S. PATENT DOCUMENTS

| | | |
|---|---|---|
| 6,120,433 A | 9/2000 | Mizuno et al. |
| 7,507,199 B2 | 3/2009 | Wang et al. |
| 10,743,947 B2 | 8/2020 | Peine |
| 2003/0013949 A1 | 1/2003 | Moll et al. |
| 2007/0021738 A1 | 1/2007 | Hasser et al. |
| 2009/0048611 A1 | 2/2009 | Funda et al. |
| 2009/0192519 A1 | 7/2009 | Omori |
| 2009/0326322 A1 | 12/2009 | Diolaiti |
| 2010/0161129 A1 | 6/2010 | Costa et al. |
| 2010/0228265 A1 | 9/2010 | Prisco |
| 2011/0015569 A1 | 1/2011 | Kirschenman et al. |
| 2011/0071543 A1 | 3/2011 | Prisco et al. |
| 2011/0202068 A1 | 8/2011 | Diolaiti et al. |
| 2011/0238010 A1 | 9/2011 | Kirschenman et al. |
| 2012/0059391 A1 | 3/2012 | Diolaiti et al. |
| 2012/0289782 A1 | 11/2012 | Viola |

(Continued)

OTHER PUBLICATIONS

European Examination Report issued in corresponding European Application No. 15793431.6 dated May 26, 2021, 5 pages.

(Continued)

*Primary Examiner* — Tammie K Marlen

(57) ABSTRACT

The present disclosure is directed to a robotic surgical system. The robotic surgical system includes at least one robot arm, a camera, and a console. The console includes a first handle, a second handle, and a selector switch configured to select between a robotic control mode and a camera control mode. In the system the first handle or the second handle control the at least one robot arm in the robotic control mode and the first handle and the second handle control the camera in the camera control mode.

16 Claims, 4 Drawing Sheets

(56) References Cited

U.S. PATENT DOCUMENTS

2013/0310847 A1    11/2013    Niemeyer

OTHER PUBLICATIONS

Extended European Search Report dated Feb. 25, 2022 corresponding to counterpart Patent Application EP 21207093.2.
Extended European Search Report corresponding to counterpart European Patent Appln. No. EP 15 79 3431.6 dated Dec. 20, 2017, 7 pages.
Chinese First Office Action corresponding to counterpart Patent Application CN 201580025333.2 dated Jul. 30, 2018.
Australian Examination Report No. 1 corresponding to counterpart Patent Appln. AU 2015259635 dated Jan. 18, 2019, 5 pages.
Japanese Office Action corresponding to counterpart Patent Application JP 2016-567614 dated Jan. 30, 2019.
Indian Office Action issued in corresponding Indian Application No. 201617039715 dated May 5, 2020, 6 pages.
International Search Report issued in corresponding PCT/US2015/029427 dated Aug. 11, 2015, 7 pages.
First Examination Report issued in corresponding counterpart European Application No. 15 793 431.6 dated Sep. 21, 2020, 5 pages.
Chinese Second Office Action dated Jul. 5, 2022 corresponding to counterpart Patent Application ON 201910603607.1.

HANDLE PUSHED TOWARD BACK OF CONSOLE

HANDLE PULLED TOWARD FRONT OF CONSOLE

SYSTEMS AND METHODS FOR CONTROLLING A CAMERA POSITION IN A SURGICAL ROBOTIC SYSTEM

CROSS REFERENCE TO RELATED APPLICATIONS

This application is a continuation of U.S. patent application Ser. No. 15/310,476, filed on Nov. 11, 2016 (now U.S. Pat. No. 10,743,947), which is a U.S. National Stage Application filed under 35 U.S.C. § 371(a) of International Patent Application No. PCT/US2015/029427, filed May 6, 2015, which claims the benefit to U.S. Provisional Patent Application No. 61/993,379, filed May 15, 2014, the entire disclosure of each of which is incorporated by reference herein.

BACKGROUND

Surgical robotic systems make it easier and less tiresome for surgeons to perform minimally invasive surgery. During traditional laparoscopic surgery surgeons manually oriented, moved, and actuated surgical instruments in the patient during surgery. Surgeons had to maneuver, hold, and activate the surgical instruments in awkward positions for prolonged periods causing discomfort and fatigue. Surgical robotic systems have a separate console and input device that the surgeon could manipulate to direct the motorized movement and actuation of surgical instruments to reduce discomfort and fatigue.

During a surgical procedure, the surgeon may receive visual feedback of an operative site through an endoscopic or a laparoscopic camera that is inserted through a surgical port into the patient. The control of the camera motion had been accomplished using methods such as voice control ("pan left", "pan down", "zoom in", etc.), tracking the surgeon's eyes as the surgeon looked at an endoscopic image on a display screen, or by using a separate input controller such as a multi-axis force sensor similar to a three-dimensional mouse (push left, right, up, or down to pan and push or pull to zoom).

In view of the foregoing, there is a need for a camera motion control scheme that allows a user to quickly and simply move the camera and/or change the viewing angle during a surgical procedure.

SUMMARY

A robotic surgical system is provided in an aspect of the present disclosure. The robotic surgical system includes at least one robot arm, a camera, and a console. The console includes a first handle, a second handle, and a selector switch configured to select between a robotic control mode and a camera control mode. In the system the first handle or the second handle control the at least one robot arm in the robotic control mode and the first handle and the second handle control the camera in the camera control mode.

In embodiments, the robotic surgical system also includes a control unit configured to control the at least one robot arm based on a signal from the console.

In some embodiments, the console includes a first motor configured to control the first handle and a second motor configured to control the second handle. Upon activation of the camera control mode, the first handle and the second handle enter a position control state in which the first motor maintains a set position of the first handle and the second motor maintains a set position of the second handle. After the first handle is moved by a user, the first motor returns the first handle to the set position of the first handle and after the second handle is moved by a user, the second motor returns the second handle to the set position of the second handle.

In other embodiments, the console includes a controller configured to control operation of the robotic surgical system. When the camera control mode is selected, the controller records a first set point for the first handle and a second set point for the second handle. The controller also creates a first dead zone around the first set point and a second dead zone around the second set point. A camera function is performed by the camera when both the first handle is moved past the first dead zone and the second handle is moved past the second dead zone. The camera function may be a movement of the camera and a velocity of the camera movement is based on a distance between: (i) a first handle position and the first set point; and (ii) a second handle position and the second set point. The camera function may include one of pan, focus, mechanical zoom, digital zoom, or switching between viewing modes.

A method for controlling a camera in a robotic surgical system having a console with a first handle, a second handle, and a selector switch is also provided in an aspect of the present disclosure. The method includes activating the selector switch to transition the robotic surgical system from a robotic control mode to a camera control mode. The method also includes setting a first set point for the first handle and a first dead zone around the first set point and setting a second set point for the second handle and a second dead zone around the second set point. A camera function is performed when both the first handle is moved past the first dead zone and the second handle is moved past the second dead zone.

In some embodiments, the camera function includes one of pan, focus, mechanical zoom, digital zoom, or switching between viewing modes. The camera function may be a movement of the camera and a velocity of the camera movement is based on how far past the first set point the first handle is moved and how far past the second set point the second handle is moved.

In other embodiments, the method includes maintaining the first handle at the first set point when a force is not applied to the first handle and maintaining the second handle at the second set point when a force is not applied to the second handle.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
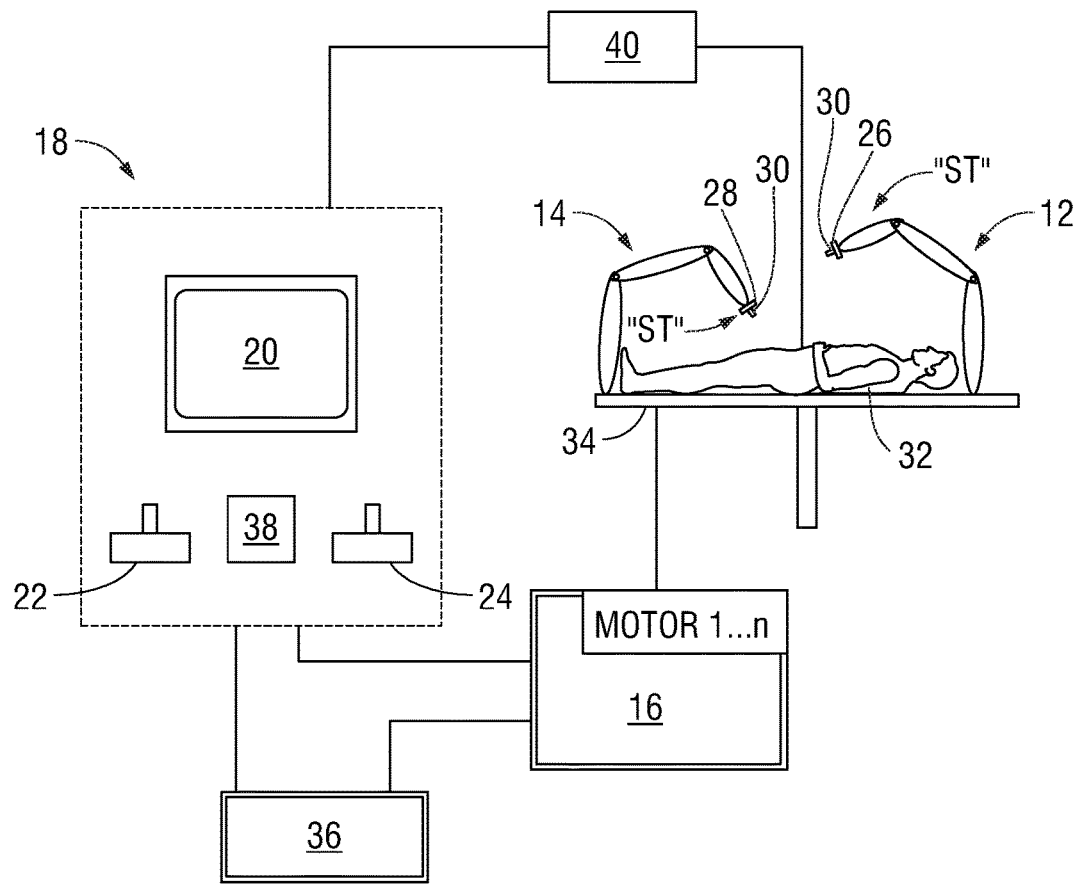
FIG. 1 is a system block diagram of a robotic surgical system in accordance with an embodiment of the present disclosure.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various haptic sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

The surgical system may also employ an endoscopic or laparoscopic camera inserted into the patient through a surgical port into the patient, which may in some instance be an abdominal or thoracic cavity. The master handles may be used by the surgeon to control camera functions, such as pan and zoom.

Referring initially to FIG. 1, a surgical robotic system is shown generally as system 10 and generally may include a plurality of robot arms 12, 14; a control device 16; and an operating console 18 coupled with control device 16. Operating console 18 may include a display device 20, which may be set up in particular to display two-dimensional (2D) images or three-dimensional (3D) images; and master handles 22, 24, by means of which a person (not shown), for example a surgeon, may be able to telemanipulate robot arms 12, 14 in a first operating mode.

Each of the robot arms 12, 14 may include a plurality of members, which are connected through joints, and an attaching device 26, 28, to which may be attached, for example, a surgical tool "ST" supporting an end effector 30, in accordance with any one of several embodiments disclosed herein, as will be described in greater detail below.

Robot arms 12, 14 may be driven by electric drives (not shown) that are connected to control device 16. Control device 16 (e.g., a computer) may be set up to activate the drives, in particular by means of a computer program, in such a way that robot arms 12, 14, their attaching devices 26, 28 and thus the surgical tool (including end effector 30) execute a desired movement according to a movement defined by means of master handles 22, 24. Control device 16 may also be set up in such a way that it regulates the movement of robot arms 12, 14 and/or of the drives.

System 10 may be configured for use on a patient 32 lying on a patient table 34 to be treated in a minimally invasive manner by means of end effector 30. System 10 may also include more than two robot arms 12, 14, the additional robot arms likewise being connected to control device 16 and being telemanipulatable by means of operating console 18. A medical instrument or surgical tool (including an end effector 30) may also be attached to the additional robot arm. System 10 may include a database 36, in particular coupled to with control device 16, in which are stored, for example, pre-operative data from patient/living being 32 and/or anatomical atlases.

The console 18 may include a selector switch 38 to switch the console from a robotic control mode to a camera control mode. In the robotic control mode, master handles 22, 24 control operation of the robot arms 12, 14 and/or end effector 30. Upon activation of the selector switch 38, the console switches to the camera control mode and master handles 22, 24 may be used to control a camera 40. Exemplary cameras that may be used with embodiments of the present disclosure include, but are not limited to, those mentioned in U.S. patent application Ser. No. 13/442,009 entitled "TWIN CAMERA ENDOSCOPE" filed on Apr. 9, 2012 (now U.S. Patent Publication No. US20120289782. The selector switch 38 may be a button or combination of buttons on the master handles 22, 24, a foot pedal, a voice recognition system capable of discerning a recognized voice command, or any other device capable of recognizing an action by a user and providing a signal to the console 18 to enter the camera control mode.

Figure 2:
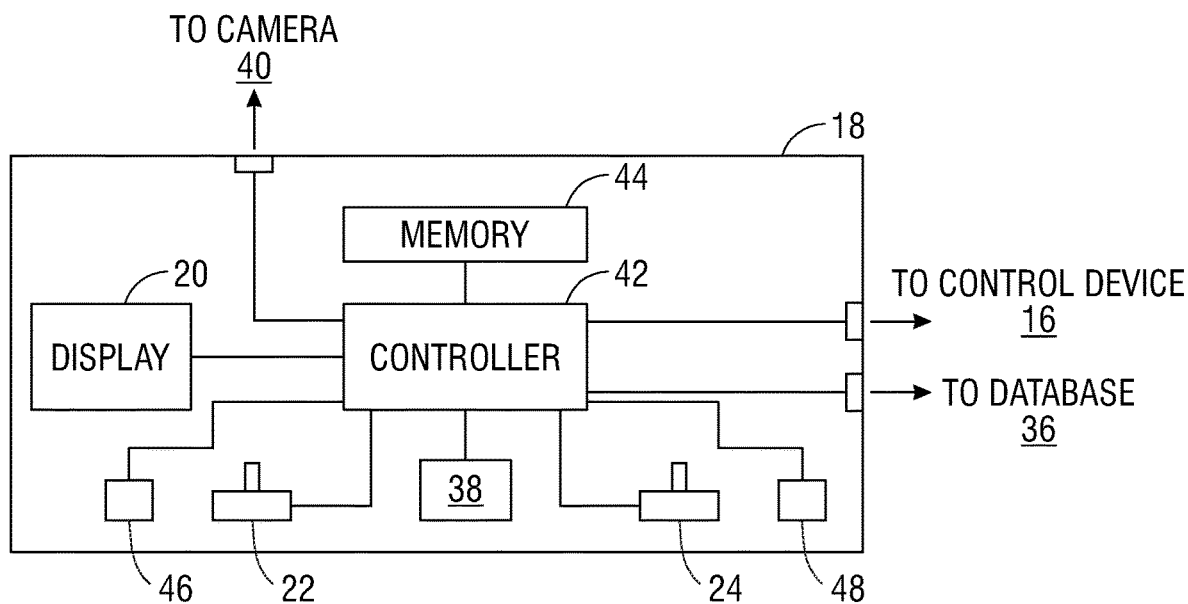
FIG. 2 is a system block diagram of the console of FIG. 1.

FIG. 2 is a system block diagram of the console 18 of FIG. 1. As described above, console 18 includes a display 20, master handles, 22, 24, and a selector switch 38. Console 18 also includes a controller 42 and a memory 44. Controller 42 receives various input signals from the control device 16, master handles 22, 24, database 36, selector switch 38, and camera 40. Controller 42 processes the input signals according to algorithms stored in memory 44 and provides output signals to control device 16, display 20, camera 40, and motors 46, 48.

Operation of the camera control mode will be discussed while making reference to FIGS. 3A-3L in conjunction with FIGS. 1 and 2. Upon entering camera control mode, one or more of the master handles 22, 24 may enter into a position control state from a non-position control state, such as a torque control state. The position control state may be entered by applying power to one or more of motors 46, 48 to maintain the position of all or some of the joints of the respective master handles 22, 24 at the angles observed when the user activated the selector switch 38 to enter into the camera control mode. Entering the position control state may cause the master handles 22, 24 or specific axes of motion of the master handles 22, 24 to be "frozen" in place. The controller 42 records a frozen set point 50a, 50b for each master handle 22, 24. While the master handles 22, 24 can be pushed away from the "frozen" set point 50a, 50b when at least a predetermined minimum force is applied, the master handles 22, 24 may return back to the "frozen" set point position when the applied force is reduced. The master handles 22, 24 therefore may act like they are tied to the set point by virtual springs 52 (FIG. 3A) in the XYZ directions (not shown) and virtual torsion springs in the roll, pitch, and yaw (RPY).

Each robot arm 12, 14 and end effector 30 may remain connected to each master handle 22, 24 that is entered into the position control state, but the motion scaling factor for the translation and/or orientation may be set to a larger value (e.g. 100:1 to 1000:1 instead of 3:1 to 5:1). The motion of the one or more master handles 22, 24 switched to the camera control mode may still cause the surgical instruments associated with the respective master handles 22, 24 to move as in the robotic control mode, but the motions of the surgical instrument may be smaller for master handles 22, 24 when they are switched to the camera control mode than for those in the robotic control mode due to the scaling factor change. In some instances, different axes may have their scaling factors remain unchanged or adjusted by different amounts. For example, if the orientation axes and gripper axis of the handle remain at 1:1 scaling, the surgeon would still be able to control the fine motion of the instrument and grasping force of the jaws while in the camera control mode.

To control the camera position, the surgeon may displace one or more of the master handles 22, 24 switched to the camera control mode in the XYZ directions away from the frozen set point 50a, 50b, pressing against the virtual springs 52 caused by the position control of each joint. The camera may then pan in the direction that the surgeon pushes the one or more master handle 22, 24. If two of the master handles 22, 24 are switched into the camera control mode then the surgeon may be required to push both of the master handles 22, 24 in the same direction to pan the camera. For example, if the surgeon pushes both master handles 22, 24 up, the camera pans up. If more than two master handles are switched into the camera control mode, then the surgeon may be required to push a predetermined number of the handles in the same direction to pan the camera.

Figure 3A:
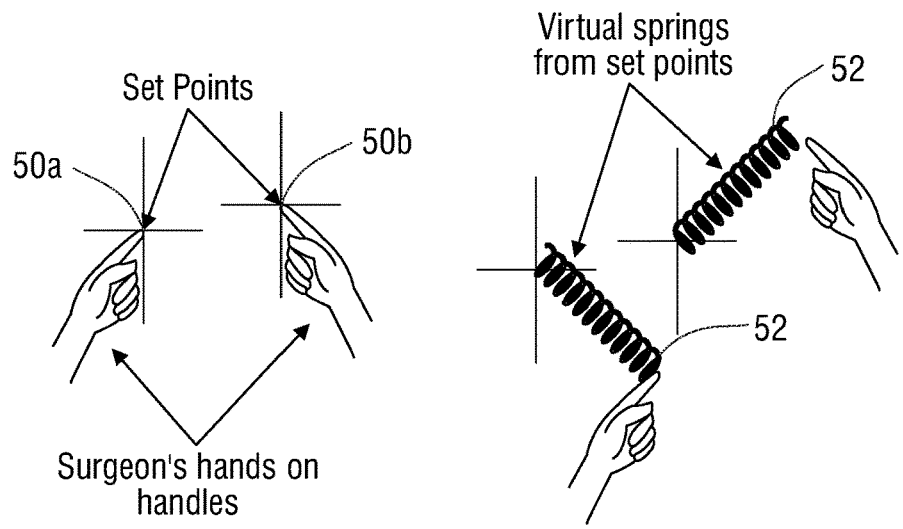
FIGS. 3A-3L depict motions used to control the endoscopic camera of FIG. 1.
Figure 3B:
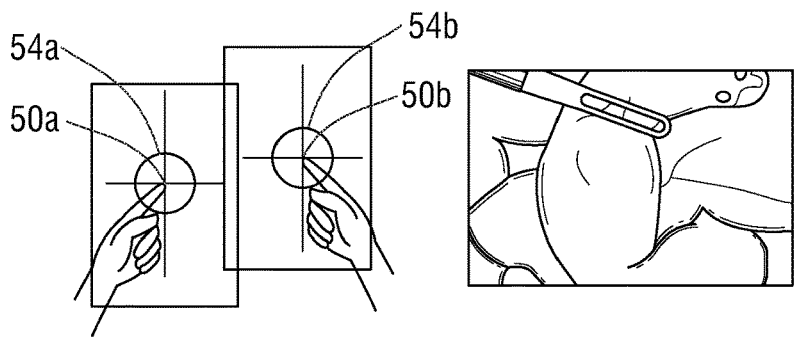
Figure 3C:
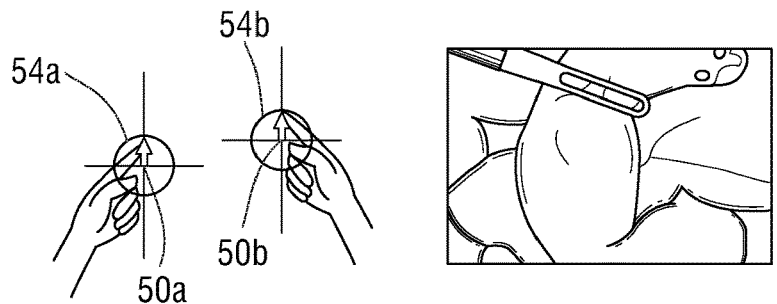
Figure 3D:
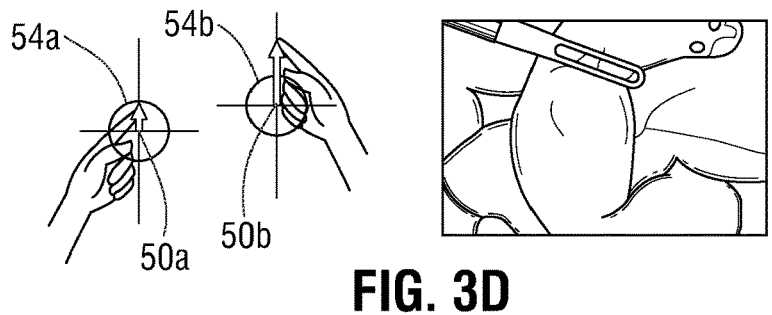

The examples described herein with regard to FIGS. 3B-3L relate to the situation in which an input device with two handles, has both handles switched to the camera control mode, but in other situations an input device may have the same or a different number of input device handles and may have the same or a different number of its input device handles switched to the camera control mode. During the camera control mode, the controller 42 creates a virtual "dead zone" 54a, 54b around the frozen set point 50a, 50b for each master handle 22, 24. (See FIG. 3B.) The surgeon would have to displace the handle beyond this dead zone to cause the camera to move. For instance, as shown in FIG. 3C, both the left hand and the right hand displace the master handles 22, 24 within the dead zone 54a, 54b resulting in no movement of the camera. In FIG. 3D, the left hand moves one of the master handles within the dead zone 54a while the right hand moves the other master handle past the dead zone 54b. Such action still results in no movement of the camera 40 because both master handles 22, 24 have not been moved past the dead zones 54a, 54b. This may minimize accidental motion and slow drifting due to noise or small offsets.

Figure 3E:
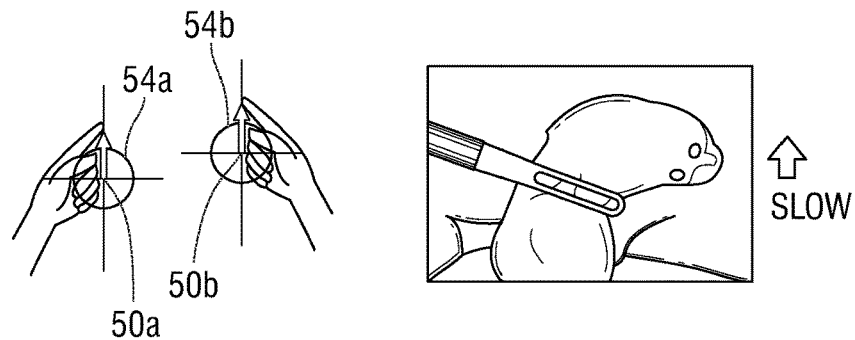
Figure 3F:
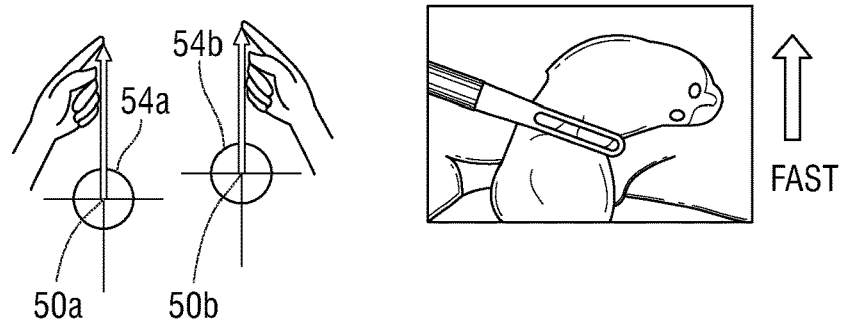
Figure 3G:
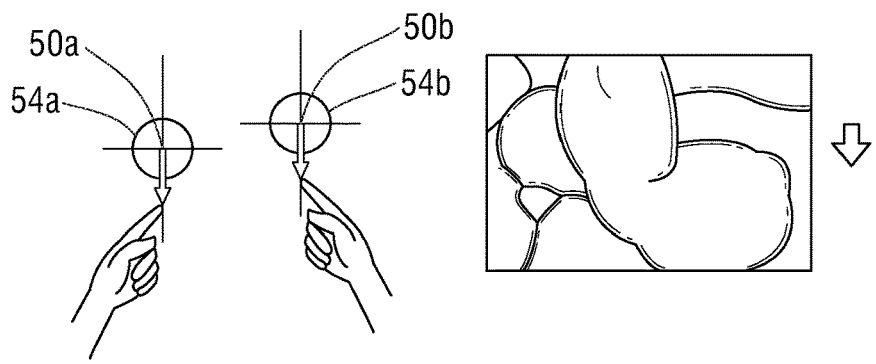
Figure 3H:
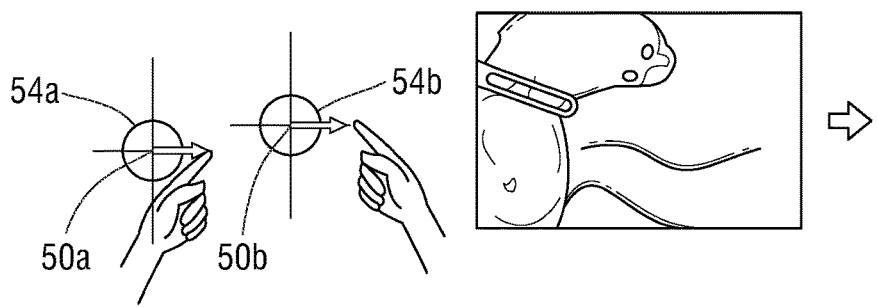
Figure 3I:
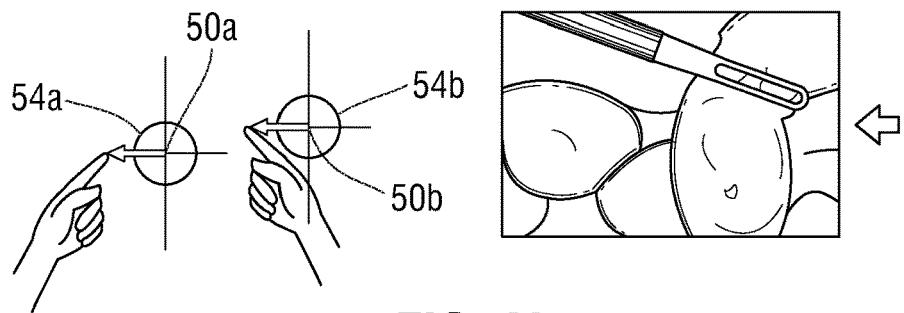
Figure 3J:
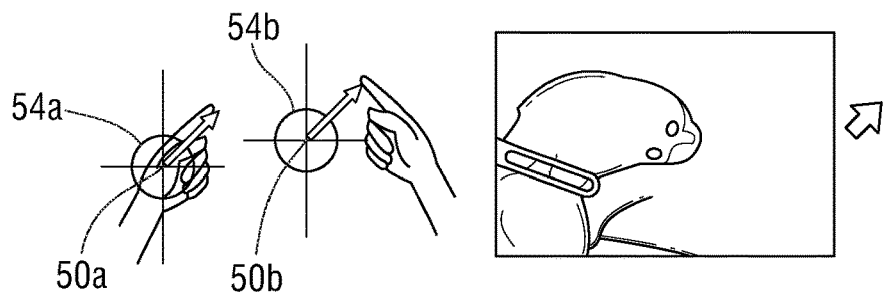
Figure 3K:
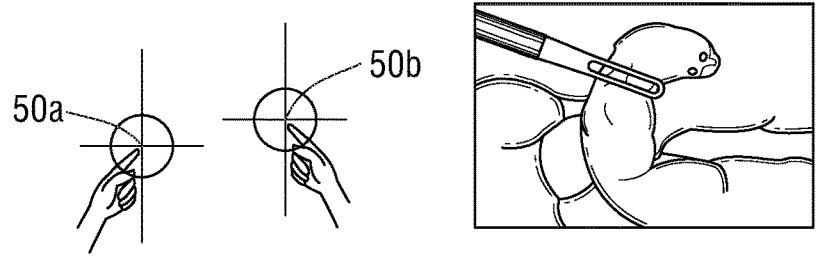
Figure 3L:
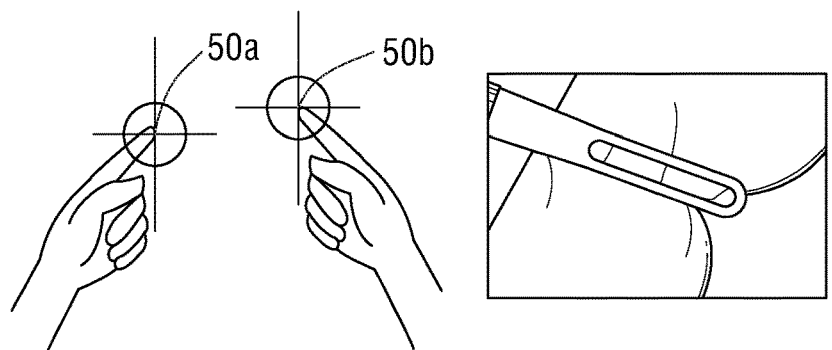

When both master handles 22, 24 are moved past the dead zone 54a, 54b, the camera 40 pans in the direction the master handles 22, 24 are moved. For instance in FIGS. 3E and 3F, the camera 40 pans upward. The speed of the panning motion may be related to how far away from the set point 50a, 50b the surgeon pushes the master handles 22, 24. As shown in FIG. 3E, the master handles 22, 24 are pushed a relatively small distance away from the set points 50a, 50b resulting in a relatively slow panning operation of the camera 40. In FIG. 3F, the master handles 22, 24 are pushed a relatively large distance away from the set points 50a, 50b resulting in a relatively fast panning operation of the camera 40. If the surgeon pushes the master handles 22, 24 down, the camera may pan down as shown in FIG. 3G. In some instances the motion may require the surgeon to move master handles 22 and 24 down (one handle with each of the surgeon's hands) to make the control more robust and less susceptible to inadvertent movement of just one handle. Similarly, displacing master handles 22 and 24 right may pan the camera 40 right (see FIG. 3H), moving master handles 22 and 24 left may pan the camera 40 left (see FIG. 3I), and moving master handles 22 and 24 diagonally may pan the camera 40 diagonally (see FIG. 3J).

The surgeon may be able to zoom the camera 40 by pushing master handles 22 and 24 toward or into the console 18 or pulling master handles 22 and 24 away from the console 18. Zooming the camera 40 may be accomplished by moving the camera 40 closer to or away from an object such as tissue, but it could also be done using a motorized lens on the camera. The rotation of the camera 40 may be controlled by differentially moving the master handles 22, 24 up and down. To rotate the image clockwise, the surgeon may push the master handle 22 down and the master handle 24 up. Counterclockwise rotation may be accomplished by moving the master handle 22 up and the master handle 24 down. Rotation of the camera 40 may also be accomplished using one of the rotational degrees of freedom of the master handles 22, 24. For example, to rotate the camera 40 image clockwise, the surgeon may roll at least one or both master handles 22, 24 clockwise about the last joint of the gimbal. Counterclockwise rotation may be done by rolling at least one, or both master handles 22, 24 counterclockwise. Other rotation schemes may also be possible, such as rotating one handle instead of two, or manipulating one or more of the handles in other ways to rotate the camera. The rolling of the master handles 22, 24 may also or instead control the focus of the camera or a mechanical zoom using lenses.

When the surgeon activates the selector switch 38 and switches out of the camera control mode, such as, in some instances, by releasing the camera button(s) or foot pedal(s), the motion scaling factor may return to a predetermined value (e.g. 3:1) or to the value that was set before being switched into the camera control mode. The console 18 may return to the non-position control state, such as a torque control state, for gravity compensation and easy manipulation of the robotic arms by the surgeon.

Other configurations may also be possible. For example, in some instances, a handle orientation change may pan the camera view. Any extra or unused degrees of freedom in the input device may be used to control one or more aspects of the camera 40. These aspects may include, but are not limited to, focus, mechanical zoom, digital zoom, or switching between viewing modes that filter the image to highlight hidden structures.

Controlling the camera 40 of a surgical robotic system 10 as described herein may improve the efficiency of surgical procedures. Efficiency may be improved, for example, by reducing the time needed to enter into the camera control mode, move the camera 40, and then resume activities in a prior mode (such as resuming manipulation of a surgical instrument in a surgical instrument manipulation mode).

Current surgical robotic systems have performed camera control mode using a position based approach. This meant that as the surgeon moved the interface handles, the camera followed the position changes of the handles. The handles therefore had to be further displaced from their original position in order to move the camera. The input device handles then remained in this displaced position when the surgeon switched out of the camera control mode. As a result, the surgeon was often required to clutch the system so the handles of the haptic interfaces could be repositioned and/or recentered in the workspace of the interface mechanism, which required an additional time consuming step. The camera control schemes described herein use a velocity control mode to move the camera 40. In this velocity control mode, the master handles 22, 24 remain in the original position that they were in when the surgeon entered the camera control mode. The master handles 22, 24 continue to remain in the original position until the surgeon leaves the camera control mode, at which time the surgeon may resume the same activities in the prior mode from the same position as when the surgeon entered the camera control mode. This may eliminate the need to clutch or reposition the master handles 22, 24 after exiting from the camera control mode.

The velocity based control mode used for camera movement also provides a more intuitive interface that is easily learnable from the control schemes of other camera systems. As a result, the time needed for surgeons to learn and feel comfortable with the camera control mode may be reduced. The surgeon may also be able to carefully control the position of the camera 40 since the camera movement speed may be controlled by how far the master handles 22, 24 are displaced from the set points. Velocity based control also may make it easier for surgeons to quickly move the camera 40 large distances by moving and holding the master handles 22, 24 further away from the set point without requiring the surgeon to reposition or clutch the master handles 22, 24. This may reduce fatigue as the surgeon's hands may need to move less in a velocity based control mode.

In the camera control schemes described herein, the haptic master handles 22, 24 need not be disengaged from controlling a surgical instrument when switching to a camera control mode. By not disengaging from instrument control, it may be possible to avoid motion discontinuities that may occur when the master handles 22, 24 are disengaged from instrument control and then reengaged into instrument control. Furthermore, if the orientation and/or gripper axes remain active with 1:1 scaling, the surgeon has the ability to maintain fine control of the instruments during the camera movement. Depending on the surgical procedure, this may allow the surgeon to be more efficient and reduce operation times. The surgeon also remains in control and can quickly react if the tissue starts to slip from the jaws of the instrument.

Although the above described embodiments require both handles to be moved in order to move the camera in a particular direction at a particular rate, in other embodiments one of the master handles may be used for a coarse movement while the other master handle may be used for fine movement.

The embodiments disclosed herein are examples of the disclosure and may be embodied in various forms. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in some embodiments," or "in other embodiments," which may each refer to one or more of the same or different embodiments in accordance with the present disclosure. A phrase in the form "A or B" means "(A), (B), or (A and B)". A phrase in the form "at least one of A, B, or C" means "(A), (B), (C), (A and B), (A and C), (B and C), or (A, B and C)".

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" includes any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other metalanguages. No distinction is made between languages which are interpreted, compiled, or use both compiled and interpreted approaches. No distinction is also made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. For instance, any of the augmented images described herein can be combined into a single augmented image to be displayed to a clinician. Accordingly, the present disclosure is intended to embrace all such alternatives, modifications and variances. The embodiments described with reference to the attached drawing figs. are presented only to demonstrate certain examples

What is claimed is:

1. A method for controlling a camera in a robotic surgical system having a console with a first handle, a second handle, a selector switch, and a controller, the method comprising:
   activating the selector switch to transition the robotic surgical system from a robotic control mode to a camera control mode;
   receiving input signals from the camera, the first handle, the second handle, and the selector switch;
   transmitting output signals to the camera, a first motor, and a second motor;
   recording the axial orientation and positioning of the first handle as a first set point, wherein the first motor is operably coupled to the first handle and automatically moves the first handle back to the first set point when the first handle is shifted away from the first set point;
   recording the axial orientation and positioning of the second handle as a second set point, wherein the second motor is operably coupled to the second handle and automatically moves the second handle back to the second set point when the second handle is shifted away from the second set point;
   repositioning the first handle to create a minimum separation between the first handle and the first set point;
   repositioning the second handle to create a minimum separation between the second handle and the second set point; and
   performing a camera function while the first handle maintains the minimum separation from the first set point and the second handle maintains the minimum separation from the second set point.

2. The method of claim 1, wherein the camera function includes pan, focus, mechanical zoom, digital zoom, or switching between viewing modes.

3. The method of claim 1, further comprising maintaining the first handle at the first set point when a force is not applied to the first handle.

4. The method of claim 3, further comprising maintaining the second handle at the second set point when a force is not applied to the second handle.

5. The method of claim 1, further comprising defining a first dead zone around the first set point based on the minimum separation from the first set point, such that no camera function can be performed while the first handle remains within the first dead zone.

6. The method of claim 1, further comprising defining a second dead zone around the second set point based on the minimum separation from the second set point, such that no camera function can be performed while the second handle remains within the second dead zone.

7. A method for controlling a camera in a robotic surgical system having a console with a first handle, a second handle, a selector switch, and a controller, the method comprising:
   activating the selector switch to transition the robotic surgical system from a robotic control mode to a camera control mode;
   receiving input signals from the camera, the first handle, the second handle, and the selector switch;
   transmitting output signals to the camera, a first motor, and a second motor;
   recording the axial orientation and positioning of the first handle as a first set point, wherein the first motor is operably coupled to the first handle;
   tethering the first handle to the first set point, such that the first handle will automatically return to the first set point after being displaced from the first set point;
   recording the axial orientation and positioning of the second handle as a second set point, wherein the second motor is operably coupled to the second handle;
   tethering the second handle to the second set point, such that the second handle will automatically return to the second set point after being displaced from the second set point;
   repositioning the first handle to create a minimum separation between the first handle and the first set point;
   repositioning the second handle to create a minimum separation between the second handle and the second set point; and
   performing a camera function while the first handle maintains the minimum separation from the first set point and the second handle maintains the minimum separation from the second set point.

8. The method of claim 7, wherein the camera function includes pan, focus, mechanical zoom, digital zoom, or switching between viewing modes.

9. The method of claim 7, further comprising maintaining the first handle at the first set point when a force is not applied to the first handle.

10. The method of claim 9, further comprising maintaining the second handle at the second set point when a force is not applied to the second handle.

11. The method of claim 7, further comprising defining a first dead zone around the first set point based on the minimum separation from the first set point, such that no camera function can be performed while the first handle remains within the first dead zone.

12. The method of claim 7, further comprising defining a second dead zone around the second set point based on the minimum separation from the second set point, such that no camera function can be performed while the second handle remains within the second dead zone.

13. A method for controlling a camera in a robotic surgical system having a console with a first handle, a second handle, a selector switch, and a controller, the method comprising:
   activating the selector switch to transition the robotic surgical system from a robotic control mode to a camera control mode;
   receiving input signals from the camera, the first handle, the second handle, and the selector switch;
   transmitting output signals to the camera, a first motor, and a second motor;
   recording the axial orientation and positioning of the first handle as a first set point, wherein the first motor is operably coupled to the first handle and automatically moves the first handle back to the first set point when the first handle is shifted away from the first set point;
   recording the axial orientation and positioning of the second handle as a second set point, wherein the second motor is operably coupled to the second handle and automatically moves the second handle back to the second set point when the second handle is shifted away from the second set point;
   defining a first dead zone around the first set point, such that no camera function can be performed while the first handle remains within the first dead zone;
   defining a second dead zone around the second set point, such that no camera function can be performed while the second handle remains within the second dead zone; and performing a camera function when both the first handle is moved past the first dead zone and the second handle is moved past the second dead zone.

14. The method of claim 13, wherein the camera function includes pan, focus, mechanical zoom, digital zoom, or switching between viewing modes.

15. The method of claim 13, further comprising maintaining the first handle at the first set point when a force is not applied to the first handle.

16. The method of claim 15, further comprising maintaining the second handle at the second set point when a force is not applied to the second handle.

* * * * *